United States Patent [19]

Mifune et al.

[11] 4,419,443
[45] Dec. 6, 1983

[54] SILVER HALIDE PHOTOGRAPHIC LIGHT-SENSITIVE MATERIAL

[75] Inventors: Hiroyuki Mifune; Yoshiharu Fuseya, both of Kanagawa; Shinpei Ikenoue, Saitama, all of Japan

[73] Assignee: Fuji Photo Film Co., Ltd., Kanagawa, Japan

[21] Appl. No.: 320,045

[22] Filed: Nov. 10, 1981

[30] Foreign Application Priority Data

Nov. 11, 1980 [JP] Japan .............................. 55/158518
May 14, 1981 [JP] Japan .............................. 56/72654

[51] Int. Cl.$^3$ .............................................. G03C 1/28
[52] U.S. Cl. .................................. 430/600; 430/603; 430/605; 430/569
[58] Field of Search ............... 430/600, 613, 614, 607, 430/599, 603, 605, 569

[56] References Cited

U.S. PATENT DOCUMENTS 2,708,161  5/1955  Jones .................................. 430/600
3,617,280  11/1971 Huckstadt et al. ................. 430/600
3,957,491  5/1976  Ohi et al. ............................ 430/600
4,001,025  1/1977  Cash .................................... 430/600
4,193,801  3/1980  Hopwood et al. .................. 430/600

*Primary Examiner*—Won H. Louie, Jr.
*Attorney, Agent, or Firm*—Sughrue, Mion, Zinn, Macpeak & Seas

[57] ABSTRACT

A silver halide photographic light-sensitive material is described comprising a support having thereon at least one silver halide emulsion layer wherein the silver halide emulsion has been chemically ripened in the presence of at least one compound containing at unit represented by the formula

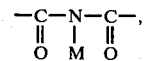

wherein M represents hydrogen, an alkali metal atom, or $NH_4$.

The silver halide photographic light-sensitive material shows high sensitivity without an accompanying increase in fog.

23 Claims, No Drawings

SILVER HALIDE PHOTOGRAPHIC LIGHT-SENSITIVE MATERIAL

FIELD OF THE INVENTION

The present invention relates to a silver halide photographic light-sensitive material, and, in particular, to a silver halide photographic light-sensitive material containing a high-speed silver halide emulsion which is chemically sensitized.

BACKGROUND OF THE INVENTION

Many methods are known for chemical sensitization of silver halide photographic emulsions (hereinafter referred to more simply as "silver halide emulsions").

For instance, (1) a sulfur sensitization process is known wherein a compound containing sulfur capable of reacting with silver ions or active gelatin is used, (2) a reduction sensitization process is known wherein a reducing substance is used, and (3) a noble metal sensitization process is known wherein a gold compound or other noble metal compounds are used. These processes can be used individually or in combination with each other.

Sulfur sensitizers that can be used include thiosulfates, thioureas, thiazoles, rhodanines, and other various compounds. Practical examples of such sensitizers are described in U.S. Pat. Nos. 1,574,944; 2,410,689; 2,278,947; 2,728,668; 3,656,955; 4,030,928; and 4,067,740.

As reduction sensitizers, stannous salts, amines, hydrazine derivatives, formamizinesulfinic acids, silane compounds, etc., can be used, and practical examples thereof are described in U.S. Pat. Nos. 2,487,850; 2,419,974; 2,518,698; 2,983,609; 2,983,610; 2,694,637; 3,930,867; and 4,054,458.

For noble metal sensitization, gold complex salts, as well as other complex salts of metals belonging to group VIII of the Periodic Table, such as platinum, iridium, and palladium, can be used, and practical examples thereof are described in U.S. Pat. Nos. 2,399,083 and 2,448,060, and British Pat. No. 618,061.

It has been strongly desired to increase the sensitivity of silver halide emulsions as high as possible, and for that purpose, attempts to increase the sensitivity of silver halide emulsions by using further new sensitizing techniques have been made.

For example, U.S. Pat. Nos. 3,625,697; 3,622,329; and 3,574,709 disclose a technique of using a well-known sensitization technique together with certain organic thioether compounds.

However, these attempts which have been made have not been completely satisfactory, and are accompanied by defects, for example, the chemical ripening can not progress to obtain sufficient sensitivity since fog increases during the progress of the chemical ripening, and the extent of the progress of chemical ripening is changed, which makes it difficult to control the extent of chemical ripening. Also, the sensitivity itself thus obtained is not always satisfactory.

SUMMARY OF THE INVENTION

An object of the present invention, therefore, is to provide a silver halide photographic light-sensitive material having a silver halide emulsion which is chemically ripened without any accompanying increase in fog.

Another object of the present invention is to provide a silver halide photographic light-sensitive material having a highly sensitized silver halide emulsion.

Other objects of the present invention will become apparent from the description below.

The objects of the invention are attained by a silver halide photographic light-sensitive material comprising a support having thereon at least one silver halide emulsion layer wherein the silver halide emulsion has been chemically ripened in the presence of at least one compound containing an unit represented by the formula

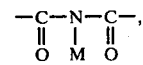

wherein M represents hydrogen, an alkali metal atom or $NH_4$.

DETAILED DESCRIPTION OF THE INVENTION

Of the compounds containing the unit represented by the formula

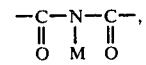

the compound represented by the following formulae (I), (II), (III) and (IV) are particularly preferred.

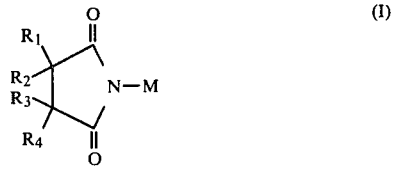

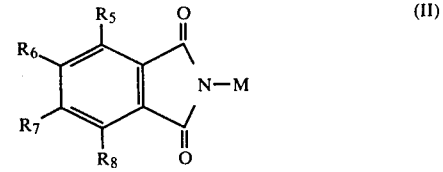

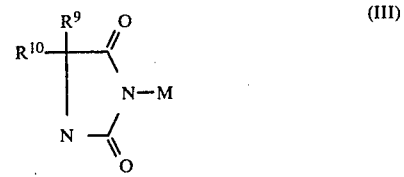

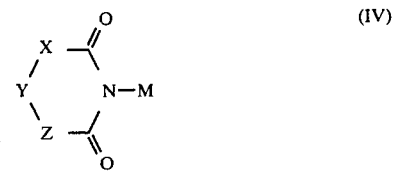

wherein M represents hydrogen, an alkali metal atom (for example, a lithium atom, a sodium atom, a potassium atom, etc.) or $NH_4$; $R_1$, $R_2$, $R_3$, $R_4$, $R_5$, $R_6$, $R_7$, and $R_8$ can each represent hydrogen, a halogen atom (for example, a chlorine atom, a bromine atom, etc.), a nitro group, a sulfo group, a carboxy group, a substituted or unsubstituted alkyl group (preferably an alkyl group having up to 8 carbon atoms, with referred examples of the substituents including a hydroxy group, a halogen atom, an acyloxy group having up to 8 carbon atoms, etc., and specific examples include a methyl group, an ethyl group, a propyl group, an isopropyl group, an amylethyl group, a hydroxyethyl group, a chloroethyl group, an acetylethyl group, etc.), a substituted or unsubstituted aryl group (preferably a monocyclic or dicyclic aryl group, with preferred examples of the substituents including a hydroxy group, a halogen atom, an alkyl group having up to 8 carbon atoms, an alkoxy group having up to 8 carbon atoms, etc., with specific examples include a phenyl group, a chlorophenyl group, a hydroxyphenyl group, an ethoxyphenyl group, etc.) or an alkoxy group (preferably an alkoxy group having up to 8 carbon atoms, and specific examples include a methoxy group, an ethoxy group, etc.); W represents —O—, —S— or $R^{11}$—N<; X represents

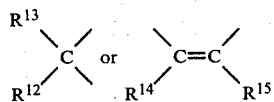

together with Y; Y represents —O—, —S—,

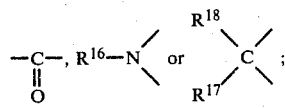

Z represents —O—, —S—, $R^{19}$—N< or

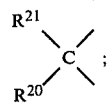

$R^9$, $R^{10}$, $R^{12}$, $R^{13}$, $R^{14}$, $R^{15}$, $R^{17}$, $R^{18}$, $R^{20}$ and $R^{21}$ can each represent hydrogen, a substituted or unsubstituted alkyl group (preferably an alkyl group having up to 8 carbon atoms, with preferred examples of the substituents including a hydroxy group, a halogen atom, an acyloxy group having up to 8 carbon atoms, and specific examples include a methyl group, an ethyl group, a propyl group, an isopropyl group, a hydroxyethyl group, a chloroethyl group, an acetylethyl group, etc.), a substituted or unsubstituted aryl group (preferably a monocyclic or dicyclic aryl group, with preferred examples of the substituents including a hydroxy group, a halogen atom, an alkyl group having up to 8 carbon atoms, an alkoxy group having up to 8 carbon atoms, etc. and specific examples include a phenyl group, a chlorophenyl group, a hydroxyphenyl group, an ethoxyphenyl group, etc.), an alkoxy group (preferably an alkoxy group having up to 8 carbon atoms. Specific examples include a methoxy group, an ethoxy group, etc.), a halogen atom (for example, a fluorine atom, a chlorine atom, a bromine atom), a sulfo group, or a carboxy group. Of these atoms or groups, hydrogen or an unsubstituted alkyl group are particularly preferred. Also, $R^{14}$ and $R^{15}$ may be connected with each other to form a condensed ring (for example, a benzene ring, etc.); $R^{11}$, $R^{16}$, and $R^{19}$ can each represent hydrogen or a substituted or unsubstituted alkyl group (preferably an alkyl group having up to 8 carbon atoms, with preferred examples of the substituents include a hydroxy group, a halogen atom, etc., and specific examples include a methyl group, an ethyl group, etc.). Hydrogen is particularly preferred for $R^{11}$, $R^{16}$, and $R^{19}$. Of the compounds represented by the general formulae (I) to (IV), the compounds represented by th general formulae (I), (III) and (IV) are preferred and the compounds represented by the general formula (I) are particularly preferred.

Specific examples of the compounds which can be used in the present invention are set forth below, but the compounds useful in the present invention are not limited thereto.

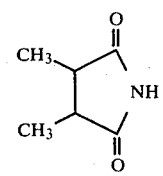 (I - 1)

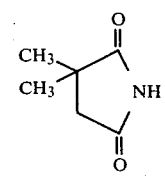 (I - 2)

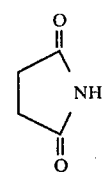 (I - 3)

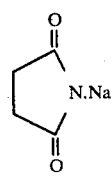 (I - 4)

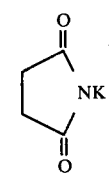 (I - 5)

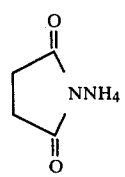 (I - 6)

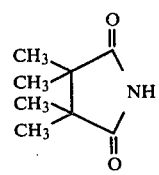 (I - 7)

-continued
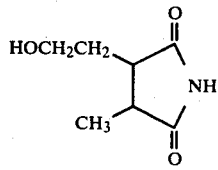 (I-8)
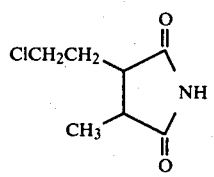 (I-9)
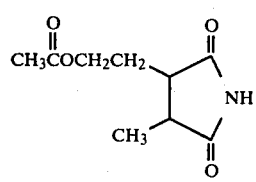 (I-10)
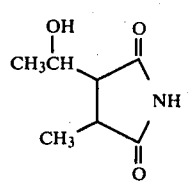 (I-11)
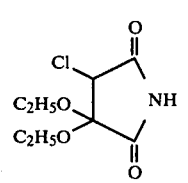 (I-12)
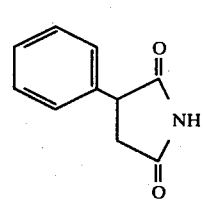 (I-13)
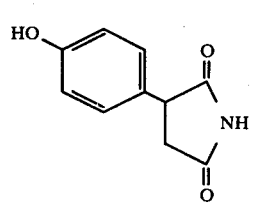 (I-14)
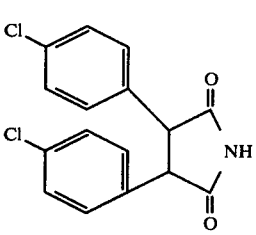 (I-15)
-continued
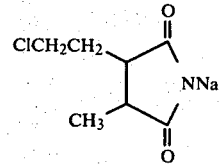 (I-16)
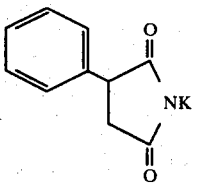 (I-17)
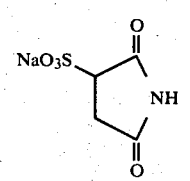 (I-18)
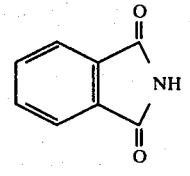 (II-1)
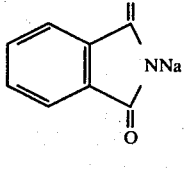 (II-2)
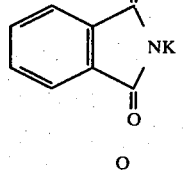 (II-3)
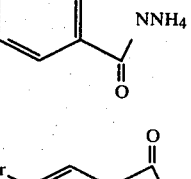 (II-4)
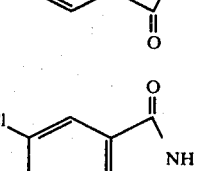 (II-5)
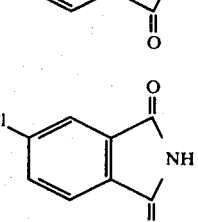 (II-6)

-continued
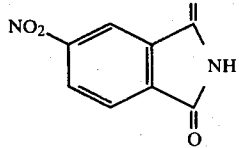 (II-7)
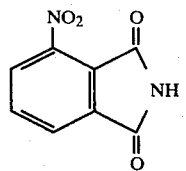 (II-8)
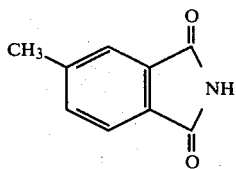 (II-9)
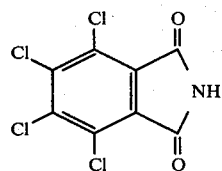 (II-10)
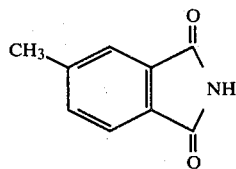 (II-11)
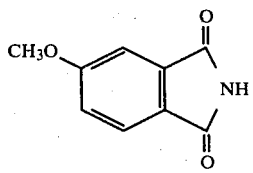 (II-12)
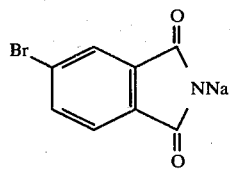 (II-13)
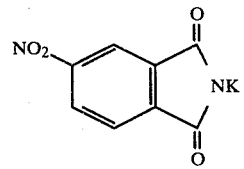 (II-14)
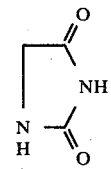 (III-1)
-continued
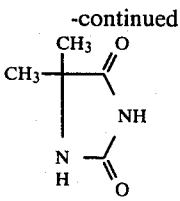 (III-2)
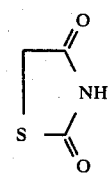 (III-3)
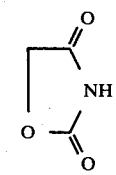 (III-4)
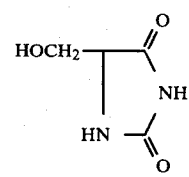 (III-5)
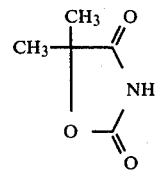 (III-6)
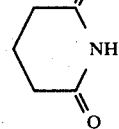 (IV-1)
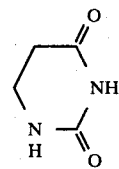 (IV-2)
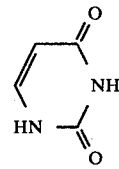 (IV-3)
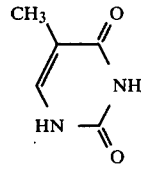 (IV-4)

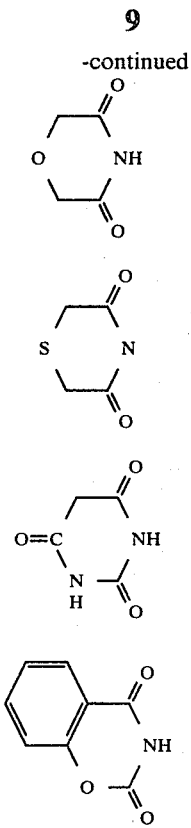

The above described compounds used in the present invention and synthesis methods thereof are known and are readily available. When the compounds according to the present invention are in the form of an alkali metal salt or an ammonium salt, these compounds can be prepared in the step of synthesis thereof or can be prepared by reacting with an alkali metal hydroxide or ammonium hydroxide just before use.

The compounds according to the present invention, for example, (1-3), (II-1), (II-10), (III-1), (III-2), (IV-1), (IV-3), (IV-4) and (IV-7) are each manufactured and sold by, for example, Wako Junyaku Co. and Aldrich Co.

The compounds represented by general formula (I) each can be easily synthesized from a succinic acid derivative represented by general formula (V) which corresponds to the compound represented by general formula (I) in the structure thereof via an intermediate represented by general formula (VI) in Reaction Scheme-1 below, according to the general synthetic methods of succinimide, for example, heating of ammonium succinate as described in Organic Synthesis, Vol. II, P 562, (1943).

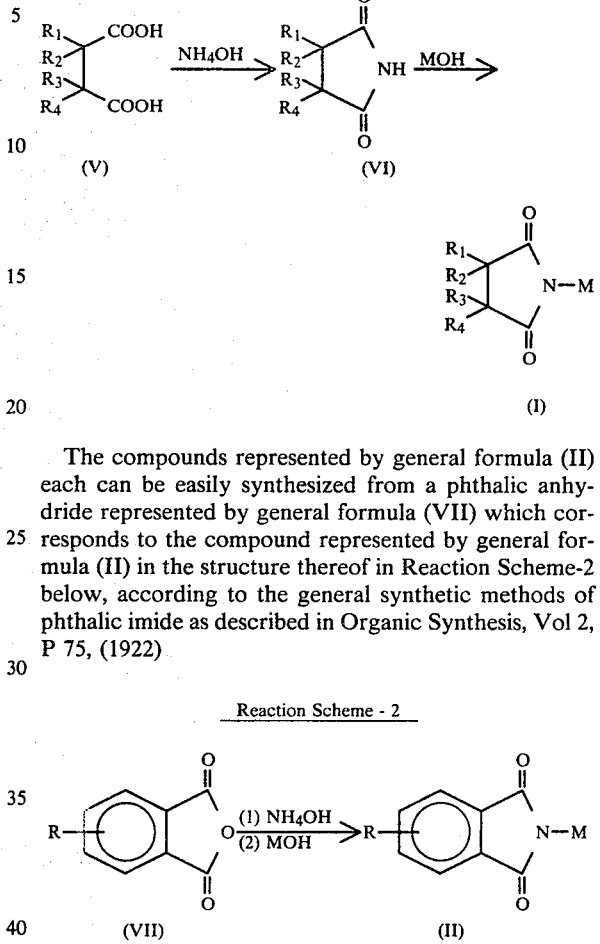

The compounds represented by general formula (II) each can be easily synthesized from a phthalic anhydride represented by general formula (VII) which corresponds to the compound represented by general formula (II) in the structure thereof in Reaction Scheme-2 below, according to the general synthetic methods of phthalic imide as described in Organic Synthesis, Vol 2, P 75, (1922)

Typical synthesis examples for synthesizing the compounds according to the present invention are described in detail below.

SYNTHESIS EXAMPLE 1

Synthesis of Compound (I-1)

1 g of 2,3-dimethylsuccinic acid (a mixture of D-, L-, and meso-isomers) was added to 10 ml of 28% aqueous ammonium solution. The mixture was heated and stirred at about 60° C. for 1 hour. After cooling, to the reaction mixture was added aqueous hydrochloric acid solution so as to neutralize, and then the mixture was extrated twice with 10 ml of ethyl acetate. The extract was concentrated to obtain 0.73 g of 2,3-dimethylsuccinimide (a mixture of D-, L, and meso-isomers).

SYNTHESIS EXAMPLE 2

Synthesis Compound (I-13)

10 g of phenylsuccinic anhydride was gradually added to 20 ml of 28% aqueous ammonium solution and the mixture was stirred for about 1 hour. To the reaction mixture was added aqueous hydrochloric acid solution so as to neutralize. After cooling, crystals thus formed were collected by filtration to obtain about 8.2 g of 3-phenylsuccinimide.

SYNTHESIS EXAMPLE 3

Synthesis of Compound (II-6)

5 g of 4-chlorophthalic anhydride was gradually added to 20 ml of 28% aqueous ammonium solution and the mixture was stirred for about 1 hour. To the reaction mixture was added aqueous hydrochloric acid solution so as to neutralize. After cooling, crystals thus formed were collected by filtration to obtain 4.2 g of 4-chlorophthalic imide.

SYNTHESIS EXAMPLE 4

Synthesis of Compound (III-3)

In a 1-liter three neck distillation flask were placed 300 ml of ethanol solution of 139 g of mono-bromo acetate (1 mole), 76 g of thiourea (1 mole) and 90 g of sodium acetate (1.1 mol), and the mixture was refluxed with heating for 4 hours. After cooling, crystals thus formed were collected by filtration to obtain an imino compound. The imino compound was added to 400 ml of 10% aqueous hydrochloric acid solution and then the mixture was heated on warm water bath for 1 hour. After cooling, crystals thus formed were collected by filtration and recrystalized from a mixing solvent of ethyl acetate and hexane to obtain 43 g of thiohydantoin having a melting point of 126° to 128° C.

SYNTHESIS EXAMPLE 5

Synthesis of Compound (III-6)

In a 5-liter three neck distillation flask were placed 1.5 l of ethanol, 92 g of metallic sodium, 472 g of ethyl α-hydroxyisobutyrate (4 mole), and 240 g of urea (4 mole). The mixture was heated and stirred on hot oil bath at 100° C. for 18 hours. After ethanol and methanol were distilled off from the reaction mixture and then 2 l of water was added therefor, the mixture was made acid with aqueous hydrochloric acid solution and then extracted twice with ethyl acetate. The extract was dried with Glauber's salt, and then filtered. The solvent was distilled off from the extract to obtain 270 g of 5,5-dimethylhydantoin having a melting point of 75° C.

SYNTHESIS EXAMPLE 6

Synthesis of Compound (IV-5)

In a 300-milliliter three neck distillation flask was placed a mixture of 50 g of diglycollic acid, 69 g of ammonium acetate. The mixture was heated on the hot oil bath at about 200° C. for about 40 minutes to obtain the melt thereof. The melt thus obtained was heated for more 10 minutes as it is. After cooling, 75 ml of water and 1 g of active carbon were added to the melt, and then the mixture thus obtained was heated and stirred at 100° C. for 30 minutes. The active carbon was filtered from the reaction mixture. After cooling, crystals thus formed were collected by filtration and recrystalized from 120 ml of methanol to obtain about 20 g of diglycollic imide having a melting point of 142° to 143° C.

The compounds according to the present invention must be present in a silver halide emulsion during a chemical ripening step in the production of a silver halide emulsion. Therefore, in the present invention, the compound is added to a silver halide emulsion in at least one step selected from a step of precipitation of silver halide grains, a physical ripening step subsequent to the precipitation step, and a chemical ripening step subsequent to the physical ripening step. Preferably, the compound is added to a silver halide emulsion prior to the chemical ripening step, e.g., during the step of precipitation of silver halide grains, or before or during physical ripening step. It is particularly preferred to previously add the compound to a vessel in which silver halide grains are being formed during the step of precipitation of the silver halide grains.

The amount of the compound represented by the general formula (I), (II), (III), or (IV) according to the present invention added to a silver halide emulsion is preferably from 0.05 to 200 g, and more preferably from 0.1 to 100 g, per mol of silver halide if added before a physical ripening step or during physical ripening step, and preferably from 0.001 to 10 g, and more preferably from 0.005 to 3 g, per mol of silver halide if added during a chemical ripening step.

It is preferred that the amount of the compound of the formulae (I) to (IV) existing finally in a silver halide emulsion layer of a silver halide photographic light-sensitive material be from 0.001 to 10 g, and more preferably from 0.005 to 3 g, per mol of silver halide.

When chemical ripening is carried out in the presence of a compound according to the present invention, the increase in fog which is usually observed according to the progress of the chemical ripening scarecely occurs, and thus a silver halide emulsion having a low level of fog and a high sensitivity can be obtained. Particularly, when the compound is added to a silver halide emulsion before or during the physical ripening step, the effect that sensitization in a chemical ripening step subsequent thereto is effectively conducted is obtained in addition to the above described effects. On the contrary, when the imide compound is added to a silver halide emulsion after the completion of the chemical ripening step, as described in U.S. Pat. Nos. 1,763,989 and 1,763,990, the above described effects are completely not obtained.

Chemical sensitizers conventionally known that can be used together with the compound according to the present invention include sulfur sensitizers, noble metal sensitizers, reducing sensitizers, etc., as described above.

With respect to the noble metal sensitizers, gold complex salts (e.g., those described in U.S. Pat. No. 2,399,083) are preferably used.

Examples of the particularly preferred gold complex salts are potassium chloroaurate, potassium aurithiocyanate, auric trichloride, and 2-aurosulfobenzothiazole methochlroride.

Combinations of two or more kinds of the conventional known chemical sensitizers, such as noble metal sensitizers, sulfur sensitizers, etc., can be used together with the compound according to the present invention.

There is no particular restriction with respect to an addition time of these chemical sensitizers except that the compound according to the present invention is present together with the conventional known chemical sensitizers during the chemical ripening step. That is, conventional chemical sensitizers can also be added to a silver halide emulsion during the formation of silver halide grains and/or during chemical ripening.

It is preferred that the amount of a sulfur sensitizer used is from $5 \times 10^{-6}$ to $10^{-2}$ mol per mol of silver halide, the amount of a noble metal sensitizer used is from $10^{-9}$ to $10^{-3}$ mol, and particularly from $10^{-8}$ to $10^{-4}$ mol, per mol of silver halide.

The silver halide for the silver halide emulsion used in the present invention can be silver bromide, silver iodobromide, silver iodochlorobromide, silver chlorobromide, silver chloride, and mixtures thereof.

There is no particular limitation on the mean grain size of the silver halide grains (when the silver halide grains are spherical or almost spherical grains, "grain size" refers to the diameter of the grain, and when the silver halide grains are cubic grains, "grain size" refers to the length of the edge, which is shown by the average based on the projected area), but it is preferred that the mean grain size be from 0.1 to 3 microns. The grain size distribution may be narrow or wide.

The silver halide grains may comprise regular crystal forms, such as cubic, octahedron or tetradecahedron, or may comprise irregular crystal forms, such as spherical and plate crystals, or further may be mixed crystal systems of such crystal forms. Also, the silver halide grains may comprise a mixture of these various crystal grains.

The silver halide grains used in the present invention may have different phases between the inside and the surface layer thereof, or may be composed of one uniform phase. Also, the silver halide grains may be those forming latent images mainly on the surface thereof, or those forming latent images mainly inside the grains.

The silver halide emulsions according to the present invention can be prepared using the processes described in, for example, P. Glafkides, *Chimie et Physique Photographique* (Paul Montel, 1967), G. F. Duffin, *Photographic Emulsion Chemistry* (The Focal Press, 1966), and V. L. Zelikman, et al., *Making and Coating Photographic Emulsion* (The Focal Press, 1964). The emulsions may be prepared by an acid process, a neutral process, an ammonia process, etc., and systems for reacting a soluble silver salt and a soluble halide that can be used include one-side mixing process, a simultaneous mixing process, or a combination thereof.

A process for forming silver halide grains in the presence of excessive silver ions (the so-called "reverse mixing" process) can be used. In one mode of the simultaneous mixing process, a process of maintaining the pAg of the liquid phase forming the silver halide at a constant value, that is, the so-called "controlled double jet" process, can be used.

According to this process silver halide emulsions having regular crystal form and almost uniform grain size are obtained. Two or more kinds of silver halide emulsions prepared separately can be used as a mixture thereof, if desired.

In the step of forming silver halide grains or the physical ripening thereof, a cadmium salt, a zinc salt, a lead salt, a thallium salt, an iridium salt or the complex salt thereof, a rhodium salt or the complex salt thereof, an iron salt or the complex salt thereof, etc., may be present in the silver halide emulsion. Also, as a silver halide solvent, ammonia, potassium thiocyanate, or thioether compound can be used.

The conditions for the formation and precipitation of silver halide grains or the physical ripening thereof that are preferred are a temperature of from 30° to 90° C. and particularly from 40° to 80° C., a pH of from 1 to 11, and particularly from 2 to 9, and a pAg of from 5 to 11, and particularly from 7.8 to 10.5.

Also, as the conditions for chemical ripening, it is preferred that the temperature be from 30° to 80° C., and particularly from 40° to 70° C., that the pH be from 3.0 to 8.5, and particularly from 5.0 to 7.5, that the pAg be from 7.0 to 9.5, and particularly from 8.0 to 9.3, and that the time thereof be from 10 to 200 minutes, and particularly from 30 to 120 minutes.

It is advantageous to use gelatin as a binder or a protective colloid for the silver halide emulsion, but hydrophilic colloids other than gelatin can also be used in the present invention. For example, gelatin derivatives, graft polymers of gelatin and other polymers; proteins such as albumin, casein, etc.; cellulose derivatives such as hydroxyethyl cellulose, carboxymethyl cellulose, cellulose sulfuric acid esters, etc.; sugar derivatives such as sodium alginate, starch derivatives, etc.; and various synthetic hydrophilic high molecular substances, for example, homopolymers and copolymers such as polyvinyl alcohol, polyvinyl alcohol partial acetal, poly-N-vinylpyrrolidone, polyacrylic acid, polymethacrylic acid, polyacrylamide, polyvinylimidazole, polyvinylpyrazole, can also be used.

The silver halide emulsions used in the present invention may contain various compounds for the purposes of preventing the occurrence of fog during the preparation, preservation, or photographic processing of the photographic materials, as well as stabilizing the photographic properties of the photographic materials. These various antifoggants and stabilizers include azoles, such as benzothiazolium salts, nitroindazoles, nitrobenzimidazoles, chlorobenzimidazoles, bromobenzimidazoles, mercaptothiazoles, mercaptobenzthiazoles, mercaptobenzimidazoles, mercaptothiadiazoles, aminotriazoles, benztriazoles, nitrobenztriazoles, mercaptotetrazoles (in particular, 1-phenyl-5-mercaptotetrazole), etc.; mercaptopyrimidines; mercaptotriazines; thioketo compounds such as oxazolinethion; azaindenes, such as triazaindenes, tetraazaindenes (in particular, 4-hydroxy-substituted(1,3,3a,7)-tetraasaindenes), and pentaazaindenes; and benzenethiosulfonic acid, benzenesulfinic acid, benzenesulfonic acid amide, etc. For example, those described in U.S. Pat. Nos. 3,954,474 and 3,982,947 and Japanese Patent Publication No. 28660/77 can be used.

In the silver halide emulsions used in the present invention, other photographic additives normally used in the art, such as gelatin hardening agents, surface active agents, spectral sensitizing dyes, polymer latexes, dyes, color couplers, color facing preventing agents, etc., can also be used.

These additives and the production of silver halide emulsions therewith are described, for example, in *Research Disclosure*, Vol. 176, pp. 22–31 (December, 1978).

The silver halide photographic material of the present invention can have on the support one or more other layers, such as a surface protective layer, interlayers, a filter layer, a subbing layer, a backing layer, an image-receiving layer, etc., in addition to the silver halide emulsion layer or layers.

Examples of supports that can be used in the present invention include cellulose acetate films, polyethylene terephthalate films, polyolefin-coated papers, and so forth.

There are no particular restrictions with respect to the compositions of these other layers (for example, with respect to binders, gelatin hadening agents, surface active agents, antistatic agents, ultraviolet absorbents, mordants, polymer latexes, lubricants, plasticizers, matting agents, adhesion improving agents, dyes, etc.), and the coating and drying processes for the silver halide emulsion layer and other layers, and the exposure and developing processes for the silver halide photographic light-sensitive materials that can be used are conventional, as described, for example, in *Research Disclosure*, Vol. 176, pp. 22–31 (December, 1978).

The following examples are intended to illustrate the present invention, but the present invention is not to be construed as being limited thereto.

EXAMPLE 1

While stirring an aqueous gelatin solution containing potassium iodide and potassium bromide at 70° C., an aqueous solution of potassium bromide and an aqueous solution of silver nitrate were simultaneously added to the gelatin solution to prepare a silver iodobromide emulsion (iodide: 5 mol%) having a mean grain size of about 0.8 micron.

The silver halide emulsion was cooled, set, and washed with water to remove unnecessary salts in a conventional manner and adjusted to desired pH value and pAg value (pH 6.5 and pAg 8.9). To the silver halide emulsion, the compound according to the present invention was added as shown in Table 1 below, and the emulsion was heated to 60° C., chemically ripened with the addition of 6.8 mg per mol of silver of sodium thiosulfate and 2.8 mg per mol of silver of potassium chloroaurate, and sampled as shown in Table 1 below.

After adding to each of the silver halide emulsions the following sensitizing dye, stabilizer, color coupler, gelatin hardening agent, and coating aid in the following amounts, the silver halide emulsion was coated on a cellulose acetate film support in an amount of 5.5 g per square meter of the support as silver and dried.

| | |
|---|---|
| Sensitizing dye: 5,5'-dichloro-3,3'-di(λ-sulfopropyl)-9-ethyloxacarbocyanine sodium salt. | 5.5 mg/m$^2$ |
| Stabilizer: 4-hydroxy-6-methyl-1,3,3a,7-tetraazaindene | 35 mg/m$^2$ |
| Coupler: 1-(2,4,6-trichlorophenyl)-3-[3-(2,4-di-t-amylphenoxy)acetamido]benzamido-5-pyrazolone | 0.7 g/m$^2$ |
| Gelating hardening agent: 2,4-dichloro-6-hydroxy-s-triazine | 15 mg/m$^2$ |
| Coating aid: sodium dodecylbenzenesulfonate | 75 mg/m$^2$ |

Each of these samples was exposed for 1/100 second through an optical wedge and subjected to the following color development processing.

| Processing Step | |
|---|---|
| 1. Color development | 3 min 15 sec (38° C.) |
| 2. Bleaching | 6 min 30 sec |
| 3. Washing | 3 min 15 sec |
| 4. Fixing | 6 min 30 sec |
| 5. Washing | 3 min 15 sec |
| 6. Stabilization | 3 min 15 sec |

The compositions of the processing solutions used in the above processing were as follows:

| | |
|---|---|
| Color Developer: | |
| Sodium nitrilotriacetate | 1.0 g |
| Sodium sulfite | 4.0 g |
| Sodium carbonate | 30.0 g |
| Potassium bromide | 1.4 g |
| Hydroxylamine sulfate | 2.4 g |
| 4-(N—Ethyl-N—β-hydroxyethylamino)-2-methylaniline sulfate | 4.5 g |
| Water to make | 1 l |
| Bleaching Solution: | |
| Ammonium bromide | 160.0 g |
| Aqueous ammonia (28%) | 25.0 ml |
| Ethylenediaminetetraacetic acid sodium iron salt | 130 g |
| Glacial acetic acid | 14 ml |
| Water to make | 1 l |
| Fixing Solution: | |
| Sodium tetrapolyphosphate | 2.0 g |
| Sodium sulfite | 4.0 g |
| Ammonium thiosulfate (70%) | 175.0 ml |
| Sodium hydrogensulfite | 4.6 g |
| Water to make | 1 l |
| Stabilizing Solution: | |
| Formalin | 8.0 ml |
| Water to make | 1 l |

The results thus obtained are set forth in Table 1 below. As is clear from the results shown in Table 1, the compounds according to the present invention have the function of suppressing an increase in fog which tends to occur during the progress of chemical ripening. Particularly, this function appears much clearer when the extent of the progress of chemical ripening is increased (i.e., when the chemical ripening is carried out for a long period of time). Therefore, it is apparent that a silver halide photographic light-sensitive material having a high sensitivity and a low level of fog is obtained by using the silver halide emulsion which is chemically ripened in the presence of the compound according to the present invention. For example, when 60 min. in Sample 1 is compared with 80 min. in Samples 4, 6 and 11, the latter shows higher relative sensitivity while maintaining the same level of fog value.

TABLE 1

| | | | Chemical Ripening Time | | | | | |
|---|---|---|---|---|---|---|---|---|
| | | | 40 Minutes | | 60 Minutes | | 80 Minutes | |
| Sample | Compound | Amount Added (g/mol Ag) | Fog | Relative Sensitivity | Fog | Relative Sensitivity | Fog | Relative Sensitivity |
| 1 | — | — | 0.10 | 76 | 0.14 | 100 | 0.19 | 116 |
| 2 | I - 3 | 0.5 | 0.09 | 78 | 0.10 | 101 | 0.13 | 117 |
| 3 | I - 1 | 0.8 | 0.09 | 75 | 0.10 | 100 | 0.13 | 115 |
| 4 | II - 1 | 0.6 | 0.10 | 76 | 0.12 | 101 | 0.14 | 114 |
| 5 | II - 13 | 0.5 | 0.09 | 75 | 0.11 | 99 | 0.14 | 113 |
| 6 | III - 1 | 1.0 | — | — | 0.12 | 102 | 0.14 | 110 |
| 7 | III - 3 | 0.3 | — | — | 0.11 | 98 | 0.13 | 108 |
| 8 | III - 6 | 1.0 | — | — | 0.12 | 100 | 0.15 | 108 |
| 9 | IV - 1 | 1.0 | — | — | 0.12 | 102 | 0.15 | 110 |
| 10 | IV - 3 | 1.0 | — | — | 0.12 | 100 | 0.15 | 108 |
| 11 | IV - 4 | 0.3 | — | — | 0.12 | 102 | 0.14 | 110 |
| 12 | IV - 5 | 1.0 | — | — | 0.12 | 98 | 0.14 | 106 |

The photographic sensitivity was shown by the relative value of the reciprocal of an exposure amount required to obtain the optical density of fog+0.20, and the sensitivity of Sample 1 chemically ripened for 60 minutes was taken as 100 in Table 1.

EXAMPLE 2

While stirring an aqueous gelatin solution containing potassium iodide and potassium bromide at 70° C., an aqueous solution of potassium bromide and an aqueous solution of silver nitrate were simultaneously added to the gelatin solution to prepare a silver iodobromide emulsion (iodide: 5 mol%) having a mean grain size of about 0.8 micron.

In this case, the compound according to the present invention was incorporated into the aqueous gelatin solution as shown in Table 2 below.

The silver halide emulsion was cooled, set and washed with water to remove unnecessary salts in a conventional manner and adjusted to desired pH value and pAg value (pH 6.5 and pAg 8.9). The emulsion was heated to 60° C., chemically ripened with addition of sodium thiosulfate and potassium chloroaurate in the amount same as described in Example 1 respectively and sampled as shown in Table 2 below.

After adding to each of the silver halide emulsions the same sensitizing dye, stabilizer, color coupler, gelatin hardening agent and coating aid, in the same amounts as were used in Example 1, the silver halide emulsion was coated on a cellulose acetate film support in the same amounts as was used in Example 1 and dried to prepare Samples 13 to 17.

These samples were exposed and subjected to color development processing in the same manner as described in Example 1.

The results thus obtained are set forth in Table 2 below. As is clear from the results shown in Table 2, where the silver halide emulsion containing the compound according to the present invention which has been added at the pre-ripening step is chemically sensitized, not only is the occurrence of fog suppressed with the progress of chemical ripening, but the sensitization is also promoted. Therefore, the presence of the compound according to the present invention during a pre-ripening step and before carrying out the chemical ripening results in a silver halide photographic light-sensitive material having a low level of fog and a much higher sensitivity.

TABLE 2

| | | | Chemical Ripening Time | | | | | |
|---|---|---|---|---|---|---|---|---|
| | | | 40 Minutes | | 60 Minutes | | 80 Minutes | |
| Sample | Compound | Amount Added (g/mol Ag) | Fog | Relative Sensitivity | Fog | Relative Sensitivity | Fog | Relative Sensitivity |
| 1 | none | — | 0.10 | 76 | 0.14 | 100 | 0.19 | 116 |
| 13 | I - 3 | 10 | 0.08 | 93 | 0.10 | 128 | 0.12 | 139 |
| 14 | III - 1 | 10 | — | — | 0.12 | 98 | 0.14 | 106 |
| 15 | III - 3 | 2 | — | — | 0.11 | 98 | 0.15 | 110 |
| 16 | IV - 1 | 10 | — | — | 0.12 | 98 | 0.14 | 105 |
| 17 | IV - 3 | 10 | — | — | 0.11 | 100 | 0.14 | 110 |

EXAMPLE 3

Samples 18, 19, and 20 were prepared in the same manner as described in Sample 13 of Example 2, except that the compounds set forth in Table 3 below were used in place of Compound I-3. The samples were exposed and subjected to color development processing in the same manner as described in Example 1. Of the results thus obtained, those obtained from the chemical ripening at 60° C. for 60 minuts are shown in Table 3. From the results shown in Table 3, it is apparent that the effects of the present invention described in Example 2 are achieved with not only the compounds represented by the general formula (I), but also the compounds represented by the general formula (II).

TABLE 3

| Sample | Compound | Amount Added (g/mol Ag) | Fog | Relative Sensitivity |
|---|---|---|---|---|
| 1 | — | — | 0.14 | 100 |
| 18 | I - 1 | 3 | 0.11 | 120 |
| 19 | II - 1 | 2 | 0.12 | 128 |
| 20 | II - 13 | 1 | 0.12 | 118 |

EXAMPLE 4

To an aqueous gelatin solution containing a small amount of sodium chloride were added simultaneously an aqueous solution of sodium chloride and potassium bromide and an aqueous solution of silver nitrate with stirring at 50° C., to provide a silver chlorobromide emulsion having a mean grain size of about 0.3 micron. In this case, the compound according to the present invention was added to the aqueous gelatin solution as shown in Table 4 below.

The silver halide emulsion was washed with water as described in Example 1 and then chemically ripened for 40 minutes at 55° C. with sodium thiosulfate and potassium chloroaurate.

After adding thereto 4-hydroxy-6-methyl-1,3,3a,7-tetraazaindene and 2,4-dichloro-6-hydroxy-s-triazine in the same amounts as used in Example 1, the silver halide emulsion was coated in the same amounts as used in Example 1 and dried. Thus, Samples 21 and 22 were prepared.

After exposure, each of the samples was developed in a Kodak D-16 developer for 3 minutes at 20° C. and then stopped, fixed, washed and dried. The results shown in Table 4 below were obtained.

As is clear from the results in Table 4 below, even in a case of a silver chlorobromide emulsion, the sensitivity can be increased without an accompanying increase in the formation of fog by adding the compound according to the present invention.

TABLE 4

| Sample | Compound | Amount Added (g/mol Ag) | Fog | Relative Sensitivity |
|---|---|---|---|---|
| 21 | none | — | 0.05 | 100 |
| 22 | I - 3 | 10 | 0.04 | 131 |

COMPARATIVE EXAMPLE 1

A silver iodobromide emulsion was prepared by the same manner as described in Sample 1 of Example 1 but the chemical ripening was carried out for 60 minutes. After adding the compound according to the present invention and the same sensitizing dye, stabilizer, color coupler, gelatin hardening agent an coating aid, in the same amounts as used in Example 1, the silver halide emulsion was coated on a cellulose acetate film support in the same amounts as used in Example 1 and dried to prepare the samples. These samples were exposed and subjected to color development processing in the same manner as described in Example 1. The results are shown in Table 5.

TABLE 5

| Sample | Compound | Amount Added (g/mol Ag) | Fog | Relative Sensitivity |
|---|---|---|---|---|
| 1 | none | — | 0.14 | 100 |
| Comp. Sample 1 | I - 3 | 0.5 | 0.14 | 100 |
| Comp. Sample 2 | " | 3 | 0.14 | 100 |

As is apparent from the results shown in Table 5, when the compound according to the present invention was added to a silver halide emulsion after the completion of the chemical ripening, no substantial change in the photographic properties (fog and relative sensitivity) was obtained.

While the invention has been described in detail and with reference to specific embodiments thereof, it will be apparent to one skilled in the art that various changes and modifications can be made therein without departing from the spirit and scope thereof.

What is claimed is:

1. A silver halide photographic light-sensitive material comprising a support having thereon at least one silver halide emulsion layer wherein the silver halide emulsion layer has been chemically-ripened in the presence of at least one compound containing a unit represented by the formula

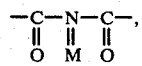

wherein M represents a hydrogen atom, an alkali metal atom, or NH$_4$, and further, wherein said compound is represented by formula (I), (II), (III) or (IV)

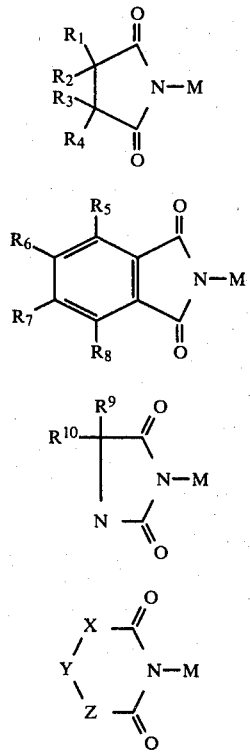

wherein M is defined as above; and R$_1$, R$_2$, R$_3$, R$_4$, R$_5$, R$_6$, R$_7$, and R$_8$ each represent a hydrogen atom, a halogen atom, a nitro group, a sulfo group, a carboxy group, a substituted or unsubstituted alkyl group, a substituted or unsubstituted aryl group, or an alkoxy group; W represents —O—, —S— or R$^{11}$—N<; X represents

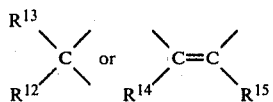

together with Y; Y represents —O—, —S—,

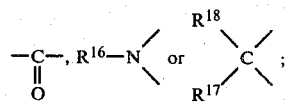

Z represents —O—, —S—, R$^{19}$—N< or

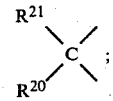

R$^9$, R$^{10}$, R$_{12}$, R$^{13}$, R$^{14}$, R$^{15}$, R$^{17}$, R$^{19}$, R$^{20}$, and R$^{21}$ each represent a hydrogen atom, a substituted or unsubstituted alkyl group, a substituted or unsubstituted aryl group, an alkoxy group, a halogen atom, a sulfo group, or a carboxy group; R$^{14}$ and R$^{15}$ may be connected to each other to form a condensed ring; and R$^{11}$, R$^{16}$, and R$^{19}$ each represent a hydrogen atom or a substituted or unsubstituted alkyl group and wherein the silver halide emulsion is sensitized with a sulfur sensitizer or noble metal sensitizer.

2. A silver halide photographic light-sensitive material as in claim 1, wherein said compound is represented by formula (I), (III) or (IV).

3. A silver halide photographic light-sensitive material as in claim 2, wherein said compound is represented by formula (I).

4. A silver halide photographic light-sensitive material as in claim 1, or 2, wherein R$^9$, R$^{10}$, R$_{12}$, R$^{13}$, R$^{14}$, R$^{15}$, R$^{17}$, R$^{18}$, R$^{20}$ and R$^{21}$ can each represent a hydrogen atom or an unsubstituted alkyl group.

5. A silver halide photographic light-sensitive material as in claim 1 or 2, wherein R$^{11}$, R$^{16}$, and R$^{19}$ each represent a hydrogen atom.

6. A silver halide photographic light-sensitive material as in claim 1, wherein said compound is added to the silver halide emulsion before completion of the chemical-ripening.

7. A silver halide photographic light-sensitive material as in claim 1, wherein said compound is added to the silver halide emulsion during a step of precipitation of silver halide grains.

8. A silver halide photographic light-sensitive material as in claim 1, wherein said compound is added to the silver halide emulsion during a physical ripening step.

9. A silver halide photographic light-sensitive material as in claim 1, wherein said compound is added to the silver halide emulsion in a chemical-ripening step.

10. A silver halide photographic light-sensitive material as in claim 1, wherein said compound is added to the silver halide emulsion before a physical ripening step or in a physical ripening step in an amount of from 0.05 to 200 g per mol of silver halide.

11. A silver halide photographic light-sensitive material as in claim 1, wherein said compound is added to the silver halide emulsion in a chemical-ripening step in an amount of from 0.001 to 10 g per mol of silver halide 12. A silver halide photographic light-sensitive material as in claim 1, wherein said compound is present in the silver halide emulsion layer in an amount of from 0.001 to 10 g per mol of silver halide.

13. A silver halide photographic light-sensitive material as in claim 1, wherein said compound is present in the silver halide emulsion layer in an amount from 0.005 to 3 g per mol of silver halide.

14. A silver halide photographic light-sensitive material as in claim 1, wherein the chemical sensitizer is a noble metal sensitizer.

15. A silver halide photographic light-sensitive material as in claim 1, wherein the chemical sensitizer is a sulfur sensitizer.

16. A silver halide photographic light-sensitive material as claimed in claim 14, wherein the noble metal sensitizer is present in an amount of from $10^{-9}$ to $10^{-3}$ mol per mol of silver halide.

17. A silver halide photographic light-sensitive material as in claim 15, wherein the sulfur sensitizer is present in an amount of from $5\times10^{-6}$ to $10^{-2}$ mol per mol of silver halide.

18. A silver halide photographic light-sensitive material as in claim 1, where the mean grain size of the silver halide grains in the silver halide emulsion is from 0.1 to 3 microns.

19. A silver halide photographic light-sensitive material as in claim 10, wherein the addition of the compound is conducted at a temperature of from 30° to 90° C., a pH of from 1 to 11, and a pAg of from 5 to 11.

20. A silver halide photographic light-sensitive material as in claim 19, wherein the addition of the compound is conducted at a temperature from 40° C. to 80° C., a pH of from 2 to 9, and a pAg of from 7.8 to 10.5.

21. A silver halide photographic light-sensitive material as in claim 11, wherein the compound is added to the silver halide emulsion at a temperature of from 30° to 80° C., a pH of from 3.0 to 8.5, and a pAg of from 7.0 to 9.5.

22. A silver halide photographic light-sensitive material as in claim 21, wherein the compound is added to the silver halide emulsion at a temperature of from 40° to 70° C., a pH of from 5.0 to 7.5, and a pAg of from 8.0 to 9.3.

23. A process for producing a silver halide photographic light-sensitive material, comprising the steps of:
(1) precipitating silver halide grains to obtain a silver halide emulsion;
(2) physically ripening the silver halide grains of the silver halide emulsion;
(3) chemically ripening the physically ripened silver halide grains of the silver halide emulsion with a sulfur or noble metal sensitizer;
(4) adding additives to the chemically ripened silver halide emulsion; and
(5) coating the silver halide emulsion onto a support; wherein a compound containing an unit represented by the formula

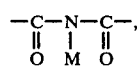

wherein M represents a hydrogen atom, an alkali metal atom, or $NH_4$, and further, wherein said compound is represented by formula (I), (II), (III) or (IV)

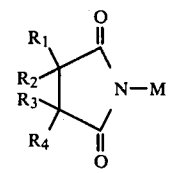 (I)

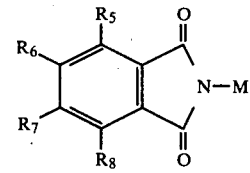 (II)

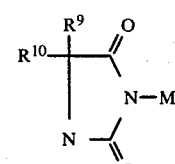 (III)

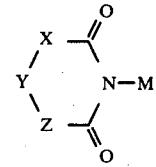 (IV)

wherein M is defined as above; and $R_1$, $R_2$, $R_3$, $R_4$, $R_5$, $R_6$, $R_7$, and $R_8$ each represent a hydrogen atom, a halogen atom, a nitro group, a sulfo group, a carboxy group, a substituted or unsubstituted alkyl group, a substituted or unsubstituted aryl group, or an alkoxy group; W represents $-O-$, $-S-$ or $R^{11}-N<$; X represents

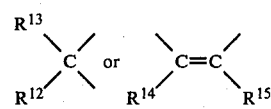

together with Y; Y represents $-O-$, $-S-$,

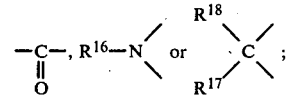

Z represents $-O-$, $-S-$, $R^{19}-N<$ or

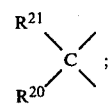

$R^9$, $R^{10}$, $R^{12}$, $R^{13}$, $R_{14}$, $R^{15}$, $R^{17}$, $R^{19}$, $R^{20}$, and $R^{21}$, each represent a hydrogen atom, a substituted or unsubstituted alkyl group, a substituted or unsubstituted aryl group, an alkoxy group, a halogen atom, a sulfo group, or a carboxy group; $R^{14}$ and $R^{15}$ may be connected to each other to form a condensed ring; and $R^{11}$, $R^{16}$, and $R^{19}$ each represent a hydrogen atom or a substituted or unsubstituted alkyl group, is added to the silver halide emulsion before completion of the chemical ripening step.

* * * * *